United States Patent [19]

Metzgar et al.

[11] 4,057,626
[45] Nov. 8, 1977

[54] PROCESS FOR DETOXIFYING INFLUENZA B VIRUS

[75] Inventors: Don P. Metzgar, Stroudsburg; Raymond H. Newhart, Pocono Summit, both of Pa.

[73] Assignee: Richardson-Merrell Inc., Wilton, Conn.

[21] Appl. No.: 731,003

[22] Filed: Oct. 8, 1976

[51] Int. Cl.$^2$ .................. A61K 39/18; C12K 7/00
[52] U.S. Cl. .................................. 424/89; 195/1.4
[58] Field of Search .......................... 195/1.4; 424/89

[56] References Cited

U.S. PATENT DOCUMENTS 3,031,378   4/1962   Ishidate et al. .................. 195/1.4

Primary Examiner—Sam Rosen
Attorney, Agent, or Firm—William J. Stein; Eugene O. Retter; George W. Rauchfuss, Jr.

[57] ABSTRACT

A detoxified influenza virus of the B group is obtained by treating an inactivated virus with formaldehyde.

4 Claims, No Drawings

PROCESS FOR DETOXIFYING INFLUENZA B VIRUS

BACKGROUND OF THE INVENTION

Influenza is an acute infectious disease in man caused by one of three types of influenza viruses. Once introduced into a susceptible community, the disease spreads rapidly from person to person by droplet transmission. Although of low mortality, influenza is marked by a high rate of morbidity.

Treatement of influenza is essentially palliative and symptomatic in nature. Sulfonamides, antibiotics and chemical agents have little, if any, effect in the treatment of this disease. Some use has been made in treating influenza with animal-immune serum or human convalescent serum, but in general, prophylactic immunization to produce a vaccine-induced immunity is the only measure readily available for the prevention of this disease.

Immunization using live viruses has received some consideration in the prevention of this disease. As a practical matter, however, such immunization has not proven effective due to the simultaneous circulation of numerous strains of influenza, each strain having its own serological and immunological characteristics. Thus, it is highly speculative to attenuate a particular strain of influenza and prepare a live virus vaccine therefrom, only to subsequently find another influenza strain to be the prevalent strain. Accordingly, immunization using a killed or inactivated virus vaccine prepared from the currently prevalent influenza strain is the most effective method known in preventing this disease.

Prior to the present invention, killed or inactivated influenza vaccines, particularly those containing type B antigen, had acquired a well-deserved reputation for producing certain undesirable side-effects. Various reasons for these reactions have been attributed to such factors as the inherent toxicity of the virus itself, allergic reactions to viral antigens prepared from egg protein used in the preparation of such vaccines, and the presence of impurities in the vaccine. This problem of vaccine toxicity has assumed even more importance in recent years, inasmuch as the amount of type B anitgen required in standard influenza vaccines has been steadily increasing. Thus, in 1972, the amount of type A anigent was increased from 400 to 700 CCA units in standard bivalent vaccines available with no appearent increase in the reactongenicity of the vaccine, (CCA refers to Chick Cell Agglutination activity per unit weight of protein nitrogen, Miller, G. L. and Stanley, W. M., J. Exp. Med. 79, 185-95, 1944). Two years later, however, when the amount of type B antigen was increased from 300 to 500 CCA units, numerous reports of patients experiencing local and systemic reactions ensued. Accordingly, numerous investigators have sought to minimize these undesirable reactions due to the increased amounts of type B antigen currently being administered.

Following a long series of investigations, applicants have discovered a relatively simple procedure for the detoxification of influenza type B antigen, which results in the elimination of much of the undesirable type B antigen reactongenicity associated with the administration of increased amounts of type B antigen. In short, treatment of an inactivated type B influenza virus with relatively high concentrations of formaldehyde for an extended period of time enables the preparation of an inactivated, detoxified type B vaccine having a reduced reactogenicity. The detoxification process described herein is readily adapted to large scale vaccine production, and is remarkably effective in eliminating to a large extent the untoward side-effects obtained with type B antigen. At the same time, this detoxification process, when practiced in accordance with the teachings of this invention, does not comprise the antigenicity or the effectiveness of either monovalent or bivalent vaccines containing type B antigen.

DESCRIPTION OF PRIOR ART

U.S. Pat. No. 3,627,873 represents the closest art known to applicants and discloses the prepration of an influenza vaccine stated to have reduced pyrogenicity. Disclosed therein is a process for the treatment of an influenza virus using a solvent selected from the group of diloweralkyl ethers and loweralkyl esters of a lower fatty acid in order to obtain an influenza vaccine of low pyrogenicity.

The prior art also teaches the detoxification of certain toxins to produce toxiods by means of formaldehyde. Thus, for example, Relyveld, Progr. Immunobiol. Standard 3, 258-63 (Karger, Basel/New York 1969) teaches the transformation of crude diphtheria toxin by means of the simultaneous action of formaldehyde and heat into a diphtheria toxoid having high antigenic capacity.

Yoskioka et al., Japan J. Microbiol., 11, 311-321 (1967), discloses the use of formalin to reduce the toxicity of a pertussis vaccine with, however, a concomitant loss in its potency.

SUMMARY OF THE INVENTION

This invention relates to a method for detoxifying an inactivated virus of the influenza B group by treating a solution of said virus with from 250 to 500 micrograms/ml. of formalin at a temperature of from about 17 to about 37° C., for a period of time ranging from about 5 to about 30 days.

In addition, this invention relates to the preparation of a detoxified, inactivated influenza B virus vaccine concentrate, and a vaccine prepared therefrom suitable for parenteral administration.

DETAILED DESCRIPTION OF THE INVENTION

Influenza viruses can be classified into one of three basic types depending upon the reactivity of the type-specific, soluble, nucleocapsid antigens which they contain. The detoxification procedure described herein, although directed primarily to influenza viruses of the B type, can also be applied to influenza viruses of the A and C types. Because of the low reactogenicity experienced with vaccines prepared from types A and C inactivated influenza viruses, the present invention is primarily concerned with a procedure for the detoxification of inactivated type B influenza virus vaccines due to the unusually high vaccine toxicity associated therewith.

The term vaccine toxicity as used herein does not refer to any poisonous or toxic substances in the inactivated influenza virus vaccine itself, but rather refers collectively to both local and systemic reactions experienced in patients receiving such vaccines. These local and systemic reactions generally appear within the first 24 hour period following injection. Local reactions caused by vaccine toxicity include pain, tenderness, erythema and induration at the site of injection. Systemic reactions caused by vaccine toxicity include headache, malaise, chills and myalgia.

Influenza viruses are subject to frequent strain variations, each with their own antigenic character. Thus, inoculation against a given influenza virus strain offers little immunity against a new strain of influenza virus that can appear the following year. Influenza viruses are generally named according to their type designation, the geographic area of their origin and the year of their occurrence. Illustrative of the various influenza B type viruses contemplated within the scope of this invention are such well-known strains as B/Lee/40, B/Md/59, B/Mass/66, B/Hong Kong/72 and the more recent B/Hong Kong/73 strain.

In accordance with the present invention, the process of detoxifying an influenza virus of the B type is achieved using either a live virus or a virus that has already been inactivated. If a live influenza B virus is utilized, the conditions for detoxification are such as to also inactivate the live virus. More particularly, however, detoxification is effected upon an influenza B virus that has already been inactivated. Still more particularly, detoxification is effected upon an influenza B virus that has been substantially purified and concentrated since the detoxification procedure requires the use of relatively high concentrations of formaldehyde in contact with the influenza virus for relatively long periods of time. Thus, as a practical matter, the detoxification of inactivated, purified and concentrated influenza B virus avoids the use of large amounts of formaldehyde necessary which would be difficult to remove in subsequent purification procedures. Additionally, here is avoided the necessity for asceptically storing large volumes of dilute virus for the relatively long periods of time required for detoxification of the virus to occur.

In order to obtain sufficient amounts of influenza B virus for inactivation, the live virus is first propagated or replicated in a suitable host. Suitable hosts include mammals, such as mice, hamsters, ferrets, mink, swine or monkeys; various tissue cultures such as those prepared from monkey, calf or hamster kidney cells; and tissue cultures prepared from various embryonic tissues, such as from chick and duck embryo or from human enbryonic lung tissue. The live chick embryo is a particularly susceptible and useful host for the replication of an influenza B virus.

Preferably, 9 to 12-day old embryonated eggs are inoculated in the amniotic or allantoic cavity with the particular strain of live influenza B virus for which a vaccine is to be prepared. The eggs are incubated at a temperature of from about 32° C. to about 37° C. for a period of two or three days. Following this period of incubation, during which the virus rapidly multiplies, the egg fluids are asceptically harvested. The egg fluids, containing live virus, are pooled, and the live virus is generally inactivated. Preferably, the egg fluids are first clarified via filtration or high speed centrifugation in order to remove any suspended particulate matter or cellular debris prior to inactivation of the virus.

Inactivation of the pooled, live influenza B virus can be achieved in a number of different ways known to the art. Thus, the virus can be inactivated by radiation, as for example, by passage through quartz tubes exposed to ultraviolet radiation. Alternatively, sonic vibrations or the use of chemical agents can be employed in order to inactivate the virus. Preferably, in accordance with this invention, the virus infected fluids are treated with a dilute solution of formaldehyde at concentrations ranging from 0.043 to 0.053% (expressed as 160 to 200 micrograms of free formalin per ml.). The virus containing fluids are permitted to remain in contact with the formaldehyde solutions for only a short period of time ranging from 16 to 24 hours at a temperature of from 17° to 37° C., during which time inactivation of the virus occurs.

Thus, in accordance with this invention, the inactivated virus is further purified and concentrated so as to remove non-viral protein and to obtain a concentration of virus that will provide sufficient viral antigen with a convenient dosage of vaccine. Purification of the inactivated influenza B virus involves procedures well-known to those skilled in the art. These purification procedures include ultra-centrifugation, adsorption onto barium sulfate, precipitation using organic solvents or ammonium sulfate and dialysis. Preferably, a combination of purification procedures is employed.

Accordingly, the inactivated influenza B virus solution is subjected to zonal ultracentrifugation employing a sucrose gradient. The appropriate zonal fraction containing the inactivated virus is further purified by adsorption onto barium sulfate. Elution of the inactivated virus is achieved using a buffered sodium or potassium citrate solution. The resulting eluate, containing the inactivated concentrated influenza B virus, is dialyzed against a sterile phosphate-buffered saline solution for approximately 24 hours to remove any inorganic salts present.

Alternatively, the final dialyzed virus concentrate can again be treated with an inactivation agent to insure complete inactivation of any live influenza B virus present. Preferably, a different inactivating agent is utilized from that previously employed. Thus, if a chemical inactivating agent such as formaldehyde was initially employed, it is desirable to ensure complete inactivation of the virus by exposure to ultraviolet radiation. The result of such a combination of procedures is to provide a substantially pure solution of inactivated influenza B virus, concentrated 20 to 50 times or more, which is safe and effective when prepared and administered as a vaccine.

Previous attempts to detoxify purified, concentrated, inactivated, influenza B virus solutions utilizing heat, trypsin digestion or chemical detoxificaion with phenol has proven unsuccessful. Surprising, however, the treatment of these solutions with more concentrated solutions of formaldehyde and for periods of time far in excess of that required for virus inactivation result in the desired detoxification of the inactivated virus solution. Vaccines prepared from such detoxified inactivated virus solutions demonstrate substantially reduced vaccine toxicity.

To applicants' knowledge the detoxification of viruses, and particularly of an influenza virus, has hithertofore been unreported. As indicated in the art cited, the conversion of certain bacterial toxins to toxoids using formaldehyde is known. However, viruses are not involved with the formation of endotoxins or exotoxins. Therefore, it appears that some other detoxification mechanism, perhaps one relating to the properties of the virus itself, is responsible for the diminished toxicity of influenza B vaccines when prepared in accordance with the present invention.

The detoxification conditions are rather critical and vary within a relatively small range. Thus, a suspension or solution of either live or inactivated influenza B virus is exposed to a formaldehyde solution at a concentration of from about 250 to about 500 micrograms of formaldehyde per ml. of virus fluid. Preferably, a concentration of from 365 to 375 micrograms of formaldehyde per ml. of virus solution is employed. The formaldehyde is permitted to remain in contact with the virus solution for a period of time ranging from about 5 to 30 days at temperatures of from about 17° to 37° C. In general, a period of from 9 to 11 days at an ambient temperature of about 25° C. is conveniently employed. The detoxification period is inversely proportional to the detoxification temperature; that is to say, higher detoxification temperatures require shorter periods of time for detoxification to occur.

After detoxification of the inactivated influenza B virus suspension or solution has occurred, excess formaldehyde is neutralized by titration with sodium bisulfite. Levels of from about 10 to 20 micrograms of formaldehyde per ml. of virus solution are permitted to remain. The residual formaldehyde serves as a preserving agent for the final vaccine prepared from the detoxified, inactivated virus solution.

The final preparation of a detoxified, inactivated influenza B virus vaccine suitable for parenteral administration does not differ substantially from those procedures known to the art. That is to say the detoxified, inactivated influenza B virus concentrate is normally diluted with isotonic saline to the appropriate potency as measured by the Chick Cell Agglutination Test (CCA). Small additional amounts of preservative, such as merthiolate, are added and the resulting vaccine tested for its sterility, pyrogenicity and such additional parameters as may be required by the Food and Drug Administration for subsequent administration to humans.

Influenza B vaccines prepared in accordance with the teachings of this invention are administered either as monovalent vaccines or administered as bivalent or trivalent influenza vaccines when combined with vaccines prepared from strains of influenza B or C viruses. If desired, these vaccines can also be administered in combination with an adjuvant such as aluminum phosphate, alum, incomplete Fruend's adjuvant or aluminum hydroxide.

Vaccines prepared in accordance with the teachings of this invention can be commerically prepared as illustrated in Example 1 with a minimum of labor and cost. It is a further advantage of this invention that no new steps or procedures need be taken and that conventional procedures already known to the art can be employed in the final processing and packaging of vaccines prepared in this manner.

Vaccines prepared in accordance with the teachings of the present invention demonstrate a marked decrease in vaccine toxicity when compared to similar non-detoxified vaccines. Thus, in the 24 hours following vaccinations, approximately 30 to 40% of the vaccinees receiving a similar non-detoxified vaccine evidenced systemic reactions of which headache, chills and malaise were particularly troublesome. Of those receiving the detoxified vaccine, only 10-15% showed any systemic reactions, and those reactions which occurred were generally milder and less severe in nature. A comparison of local reactions such as pain, tenderness, erythema and induration demonstrates similar improvements with detoxified vaccines as illustrated in Examples 2 and 3. Thus, the relatively simple treatment of an inactivated influenza B virus with formaldehyde in accordance with the process taught by the present invention results in an improved vaccine having a three-fold reduction of vaccine toxicity. This reduction in vaccine toxicity is particularly important with respect to the inoculation of small children against influenza.

The following Examples describe the preferred embodiments of this invention in greater detail and are to be considered as illustrative only and not as limiting the invention thereto.

EXAMPLE 1

Preparation of Detoxified Influenza B Virus

A total of 102,920 eleven-day-old embryonated eggs each are inoculated with 1,000 egg infectious doses of type B/Hong Kong/73 influenza virus. The infected eggs are incubated at 33° C. for 56 hours, following which the eggs are candled and the dead eggs discarded. The eggs are chilled for 18 hours at 4° C. and the virus-laden allantoic fluids are automatically harvested from each egg. Approximately 900 liters of pooled, harvested fluids are obtained and stored in chilled stainless steel tanks.

The virus-infected fluids are clarified by high speed centrifugation and stored in a stainless steel tank maintained at 25° C. Formaldehyde is added with agitation to a final concentration of 186 micrograms/milliliter, and the resulting fluids filtered through membrane filters. The clarified, filtered, formaldehyde-treated fluids are transferred to a sterile stainless steel tank and maintained at 25° C. for 24 hours in order to inactivate the virus.

The clarified, filtered, inactivated fluids are concentrated via zonal centrifugation by isopycnically banding the virus on a sucrose density gradient. The virus is recovered in 2000 ml. of the gradient fraction and diluted to a volume of 10,000 ml. with phosphate buffered saline and further purified by adsorption and elution from barium sulfate. The final volume of the barium sulfate eluate is about 13,000 milliliters. The purified virus concentrate is dialyzed for 24 hours against a sterile phosphate-buffered saline solution, filtered through a membrane filter and passed through an ultraviolet light chamber to ensure inactivation of the virus.

The final, purified, sterile concentrate is detoxified by the addition of formaldehyde to obtain a final concentration of 371 micrograms/milliliter. The purified, sterile concentrate is permitted to remain in contact with the formaldehyde at 25° C., undisturbed for a period of 10 days.

Following detoxification, the formaldehyde is neutralized with sufficient 35% sodium bisulfite solution to permit an excess of 10 micrograms/milliliter of formaldehyde to remain in the final concentrate product. The concentrate is diluted with sterile phosphate buffered saline solution to form a vaccine having a final antigenic concentration of 1000 CCA per ml. (500 CCA per dose).

EXAMPLE 2

The following data illustrates the reduced vaccine toxicity observed with the detoxified monovalent influenza B vaccine prepared in accordance with the preceding Example, when compared with a vaccine having the same potency and prepared in the same manner as Example 1 except that the virus concentrate was not detoxified by the formaldehyde treatment.

Each of the vaccines was administered to forty volunteers in a double-blind study. Local and systemic reactions were observed by trained nurse epidemolgoists 24 hours following administration. The numerical values indicate percent incidence of reactions observed expressed as mild (m) and as moderate to severe (m-s) reactions.

| Reactions | Vaccine 500 CCA | | Detoxified Vaccine 500 CCA | |
|---|---|---|---|---|
| | m | m-s | m | m-s |
| Local | | | | |
| Pain | 15 | 15 | 15 | 10 |
| Tenderness | 25 | 40 | 50 | 30 |
| Erythema | 5 | 0 | 5 | 0 |
| Induration | 15 | 10 | 5 | 10 |
| Systemic | | | | |
| Headache | 15 | 20 | 0 | 15 |
| Malaise | 15 | 25 | 10 | 0 |
| Chills | 15 | 15 | 5 | 5 |
| Myalgia | 5 | 5 | 5 | 0 |

EXAMPLE 3

The following data summarizes the results of another study illustrating the reduced vaccine toxicity observed with a different lot of detoxified monovalent influenza B vaccine, prepared essentially in accordance with the procedure of Example 1, when compared with a non-detoxified vaccine of the same derivation and having the same potency.

Each of the vaccines was administered to 46 volunteers in a double-blind study. Local and systemic reactions were observed by trained nurse epidemologists 24 hours following administration. The numerical values indicate percent incidence of reactions observed expressed as mild (m) and as moderate to severe (m-s) reactions.

| Reactions | Vaccine 500 CCA | | Detoxified Vaccine 500 CCA | |
|---|---|---|---|---|
| | m | m-s | m | m-s |
| Local | | | | |
| Pain | 0 | 0 | 4 | 4 |
| Tenderness | 43 | 30 | 39 | 30 |
| Erythema | 22 | 0 | 26 | 0 |
| Induration | 17 | 0 | 22 | 0 |
| Systemic | | | | |
| Headache | 4 | 34 | 13 | 0 |
| Malaise | 9 | 31 | 0 | 4 |
| Chills | 9 | 9 | 9 | 0 |

We claim:

1. A method of detoxifying a virus of the influenza B group which comprises treating an aqueous concentrate of said virus with from 250 to 500 micrograms of formaldehyde per ml of virus concentrate at a temperature of from 17 to 37° C. for a period of time ranging from 5 to 30 days.

2. A method according to claim 1 wherein said aqueous concentrate comprises a live virus that has been inactivated with from 160 to 200 micrograms/ml. of formaldehyde at a temperature of from 17° to 37° C. and for a period of time ranging from 16 to 24 hours.

3. A process for the preparation of a detoxified, inactivated, influenza B virus vaccine concentrate which comprises:
   a. cultivating a live influenza B virus in the allantoic fluid of embryonated chicken eggs;
   b. harvesting the allantoic fluid containing said live virus;
   c. inactivating said live virus so obtained with from 160 to 200 micrograms of formaldehyde per ml of allantoic fluid at 25° C. for 18 hours;
   d. concentrating said inactivated virus by zonal centrifugation using a sucrose density gradient;
   e. purifying said inactivated virus concentrate by adsorption and elution on barium sulfate;
   f. further purifying said inactivated virus eluate by dialysis;
   g. treating said purified virus concentrate with ultraviolet light to ensure inactivation of said virus;
   h. detoxifying said inactivated virus concentrate with formaldehyde at a concentration of 350 to 400 micrograms/ml. of said virus concentrate at a temperature of 25° C. for a period of 7 to 10 days; and
   i. neutralizing excess formaldehyde with sodium bisulfite solution to obtain a detoxified, inactivated, influenza B virus vaccine concentrate.

4. A detoxified, inactivated, influenza B virus vaccine when prepared by the process of claim 3 having a final antigenic concentration of from 600 to 1000 CCA per ml.

* * * * *